(12) United States Patent
Biedermann et al.

(10) Patent No.: US 7,018,378 B2
(45) Date of Patent: Mar. 28, 2006

(54) SCREW

(75) Inventors: Lutz Biedermann, VS-Villingen (DE);
Dezsö Jeszensky, St. Gallen (DE);
Jürgen Harms, Karlsruhe (DE);
Helmar Rapp, Deisslingen (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 129 days.

(21) Appl. No.: 10/098,937

(22) Filed: Mar. 15, 2002

(65) Prior Publication Data

US 2002/0138076 A1     Sep. 26, 2002

(30) Foreign Application Priority Data

Mar. 16, 2001  (EP) .................................... 1106711

(51) Int. Cl.
*A61B 17/56* (2006.01)

(52) U.S. Cl. .......................................... 606/61; 606/72

(58) Field of Classification Search .................. 606/61, 606/62, 59, 60, 63, 65, 66, 70, 71, 72, 73
See application file for complete search history.

(56) References Cited

U.S. PATENT DOCUMENTS

| | | | |
|---|---|---|---|
| 5,005,562 A | | 4/1991 | Cotrel ........................ 128/69 |
| 5,092,635 A | * | 3/1992 | DeLange et al. ........... 285/334 |
| 5,129,388 A | | 7/1992 | Vignaud et al. ............. 606/61 |
| 5,605,457 A | * | 2/1997 | Bailey et al. ............... 433/174 |
| 5,605,458 A | | 2/1997 | Bailey et al. ............... 433/174 |
| 5,607,304 A | * | 3/1997 | Bailey et al. ............... 433/174 |
| 5,810,818 A | | 9/1998 | Errico et al. ................. 606/61 |
| 5,817,094 A | | 10/1998 | Errico et al. ................. 606/61 |
| 6,074,391 A | * | 6/2000 | Metz-Stavenhagen et al. ........................... 606/61 |
| 6,183,472 B1 | * | 2/2001 | Lutz ........................... 606/61 |
| 6,296,642 B1 | * | 10/2001 | Morrison et al. ............. 606/61 |
| 6,454,768 B1 | * | 9/2002 | Jackson ...................... 606/61 |
| 6,485,491 B1 | * | 11/2002 | Farris et al. .................. 606/61 |

FOREIGN PATENT DOCUMENTS

| | | |
|---|---|---|
| DE | 299 03 342 U1 | 7/1999 |
| DE | 298 10 798 U1 | 12/1999 |
| DE | 199 12 364 A1 | 10/2000 |
| DE | 19912364 A1 * | 10/2000 .................. 606/61 |
| EP | 0 614 649 A1 | 9/1994 |
| TW | 351742 | 1/1999 |
| WO | WO 98/31293 | 7/1998 |
| WO | WO 00/27297 | 5/2000 |

OTHER PUBLICATIONS

Meyers Enzyklopadisches Lexikon, Mannheim, 1974, p. 302.
Product information for Medtronic Sofamor Danek; CD Horizon Legacy 5.5 Spinal System dated 2003.

* cited by examiner

*Primary Examiner*—Pedro Philogene
(74) *Attorney, Agent, or Firm*—Barley Snyder LLC

(57) ABSTRACT

An element with a thread is created, in which both partial flanks enclose a negative angle with a plane extending perpendicular to the screw axis. Further, a screw or a hook for connecting to a rod, as used in particular in spinal column surgery, is created, wherein the inner thread of a holder, to which the rod is connected, and the associated thread of a nut comprise the thread according to the invention.

5 Claims, 2 Drawing Sheets

SCREW

CROSS-REFERENCE TO RELATED APPLICATIONS

Not Applicable

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

1. Field of the Invention

The invention relates to an element to be used in spinal column or accident surgery for connecting to a rod.

2. Background of the Invention

From U.S. Pat. No. 5,129,388 a pedicle screw is known which comprises a head with a U-shaped recess defining two free legs to accommodate a rod, wherein the legs are provided with an inner thread to receive a fixing screw for fixing the rod. To prevent spreading of the legs a cap is provided embracing the legs.

From U.S. Pat. No. 5,005,562 it is known with a pedicle screw according to the preamble of Patent claim 1 to construct the inner thread and the thread of the screw cooperating with it as a saw-tooth thread, so as in this way to avoid spreading out of the two flanks by completely eliminating the radial components of the force during screwing in.

A saw or else saw-tooth thread of this kind is known from Meyer's Enzyklopäidisches Lexikon, Mannheim, 1974, page 302. From both the specifications U.S. Pat. Nos. 5,605,458 and 5,607,304, concerning implants, it is known with implants of this kind to be introduced into the body, in particular hip implants, also to construct the saw thread in such a way that the flank bearing the load is constructed not only at 90° to the thread axis but even at a negative angle. This is supposed to achieve that the connection obtained with the thread resists a radial relative movement of the connected parts and thus guarantees better fixing of the implant. From EP-A-1 128 773 a pedicle screw is known in which the inner thread of a head accommodating a rod has a negative thread and the screw cooperating with it is correspondingly constructed.

The object of the invention is to create an element of the kind initially described, which is suitable for avoiding the above described disadvantage. In particular bending up of the open ends of a mount of this kind and therefore loosening of the connection between screw and rod should be avoided.

BRIEF SUMMARY OF THE INVENTION

The present invention provides an element with a shank (1) and a holding element (2) connected to it for connecting to a rod (10), wherein the holding element (2) has a recess (4), having a U-shaped cross-section, for accommodating the rod (10) with two legs (5, 6) exposed at one end (7) and an inner thread (8) on the exposed legs (5, 6) and a screw (9) cooperating with the inner thread (8), which screw directly or indirectly acts on the rod (10), wherein on the inner thread (8) with two partial flanks (12, 13), bordering on one another, the partial flanks (12, 26) facing away from the exposed end (7) enclose a negative angle $\beta_2$ with a plane which goes in each case through the base (23) of the thread and extends perpendicular to the screw axis (3), and the screw (9) cooperating with the inner thread (8) has an outer thread matching this, and wherein the radius ($r_1$) from the centre of the screw (3) to the base (21) of the thread of the screw (9) is smaller than the radius ($r_2$) from the central axis (3) of the holding element to the tip of its spiral (22), the radius ($r_3$) from the centre of the screw (3) to the tip of the spiral (22) of the screw (9) is smaller than the radius ($r_4$) from the central axis (3) of the holding element to the base (23) of the thread of its inner thread and when screw (9) and exposed legs (5, 6) of the holding element are brought into engagement without load, when the cooperating flanks (13, 24), having the positive flank angle $\beta_1$, are adjacent to one another a gap (25) is provided between the flanks (12, 26), having the negative flank angle $\beta_2$, facing one another in each case.

This construction has the advantage that the action of force between the exposed legs and the outer thread happens in such a way that the open ends of the holding element are not pressed outwards, but instead are drawn inwards, so an intensive connection takes place between the cooperating elements.

Further features and advantages of the invention emerge from the description of the embodiment examples using the figures.

DETAILED DESCRIPTION OF THE INVENTION

Figure 1:
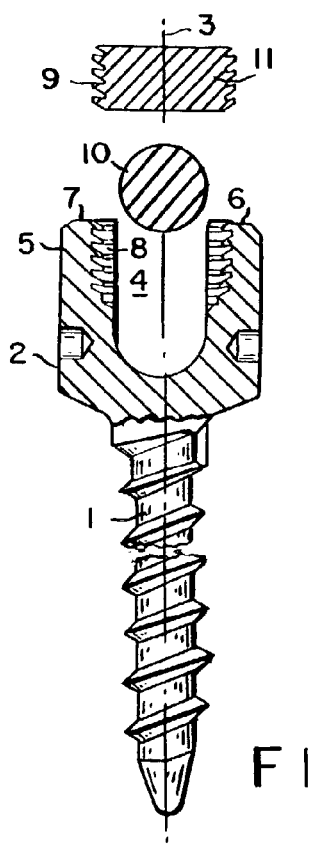
FIG. 1 shows a side view of a monoaxial pedicle screw in a bisected exploded illustration.

The pedicle screw according to FIG. 1, which can, of course, also be used generally as a bone screw or constructed as a hook, has a thread shank 1 and a head 2. The head 2 has a U-shaped recess 4, extending in the direction of the longitudinal axis 3 of the screw and with a predetermined depth. On the two thereby constructed legs 5, 6 an inner thread 8 is provided coming from the open end 7 of the legs. Matched to the inner thread 8, a screw 9 is provided, the outer thread of which is constructed in such a way that it cooperates with the inner thread 8.

In operation a rod 10, to be connected to the screw, is placed in the U-shaped recess 4 in such a way that the rod comes to rest on the base of the U-shaped recess. The screw 9 is then screwed in far enough for it to exert sufficient stopping pressure on the rod 10 located in the U-shaped recess.

Figure 2:
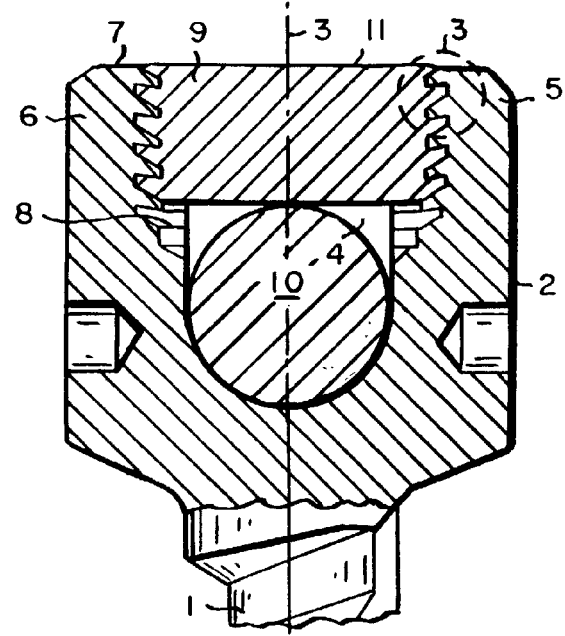
FIG. 2 shows the head of the pedicle screw shown in FIG. 1 with inserted rod and inserted nut.
Figure 3:
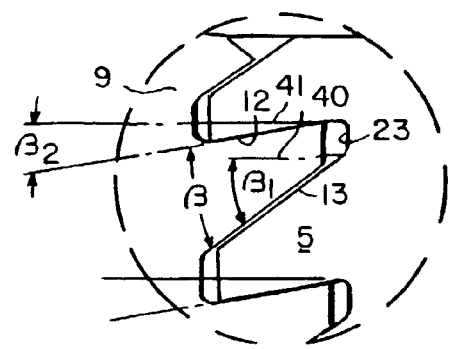
FIG. 3 shows the detail III indicated in FIG. 2 in enlarged scale.

As can be seen more clearly in FIGS. 2 and 3, the inner thread in the head 2 and the outer thread of the screw 9 are constructed in the way of a saw thread. On the surface 11 facing away from the rod 10 to be fixed the screw 9 has a slit or a hexagonal recess for the insertion of a screwdriver.

In the thread in each case two adjacent partial flanks 12, 13 form a thread pitch. The two partial flanks 12, 13 enclose the flank angle β. The flank side 13 facing the open end 7 encloses a positive angle $\beta_1$ with a plane 40, extending perpendicular to the longitudinal axis 3 and intersecting the flank side 13 on the base 23 of the thread (see FIG. 3). The partial flank 12 facing away from the open end is inclined in such a way that in the manner shown in FIG. 3 it encloses a negative angle $\beta_2$ with a corresponding plane 40. As can be seen from the figures the thread of the screw 9 is made correspondingly, so the pitches of the screw 9 engage appropriately in the inner thread 8. In screw 9 therefore each flank 26 facing the open end 7 or the surface 11 forms the negative angle $\beta_2$, which cooperates with the corresponding flank 12.

Figure 4:
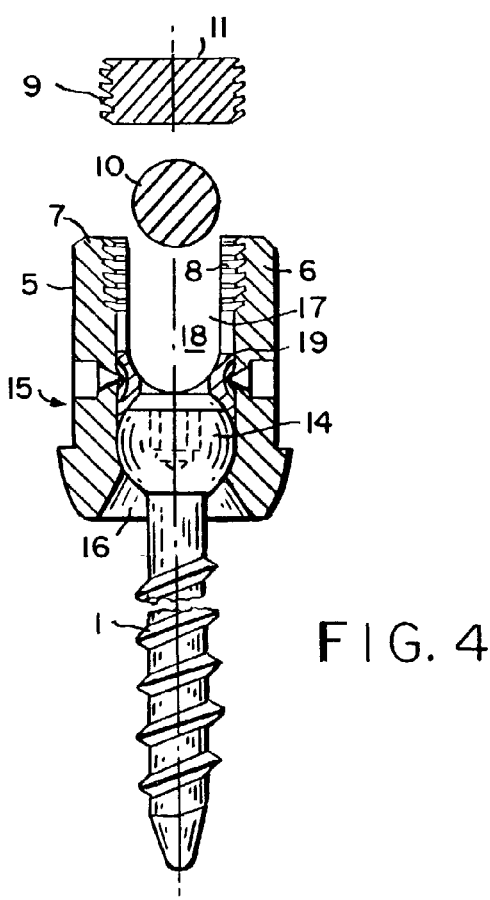
FIG. 4 shows a section corresponding to the illustration chosen in FIG. 2 for a polyaxial screw.

The embodiment shown in FIG. 4 corresponds identically in the construction of the inner thread 8 and the screw 9 cooperating with it and of the rod 10. Corresponding features are characterised by the same reference numerals.

By contrast with the first embodiment here there is a so-called polyaxial screw, in which the thread shank 1 is connected to a receiving part 15 via a spherical head 14. The receiving part has on one end an axially symmetrically aligned first bore 16, the diameter of which is larger than that of the thread section 1 and smaller than that of the head 14. The receiving part further has a coaxial second bore 17, which is open on the end located opposite the first bore and the diameter of which is large enough for the screw element to be guided through the open end with its thread section through the first bore and with the head 14 to the base of the second bore. Between the first and the second bore a small coaxial section us provided, which directly borders on the first bore and is constructed as spherical towards the open end, wherein the radius is substantially identical to the radius of the ball-segment-shaped section of the head 14. The inner thread 8 is again provided bordering on the open ends 7 of the legs 5, 6. The receiving part 15 further has a U-shaped recess 18, arranged symmetrical to the centre of the part, the base of which is directed towards the first bore, the two side legs 5, 6 of which extend towards the open end 7. Further, in the second bore 17 a pressure element is placed, which is situated on the spherical head 14. In operation the rod 10 is inserted into the U-shaped recess. Then the screw 9 is turned and screwed, in the same way as shown in FIG. 2, until it exerts a desired pressure on the pressure element 19 and therefore on the head 14 to stop it.

Instead of the above described embodiments, in which the head or the receiving part are connected in each case to a bone screw, the head or the receiving part can also be connected to a hook, as used in spinal column surgery for hooking in behind bone projections of the spinal column.

When a saw thread is spoken of above this is only supposed to characterise the direction of the partial flanks. Threads with rounded tips and rounded base, pointed threads and pointed thread base and flat thread edges and flat thread base should be also included, as is also the case with a triangular thread, round thread and trapezoidal thread.

Whereas with known screws with a metric thread, in which the screw presses on a rod in the way shown in FIG. 2, one force component acts towards the open side 11 of the screw and a second force component acts outwards in each case, with the above described thread according to the invention again one component acts towards the open end 7, but the second component acts in the direction of the longitudinal axis 3. The result of this is that the exposed legs 5, 6 are not pressed outwards, but are drawn towards the symmetrical axis.

Figure 5:
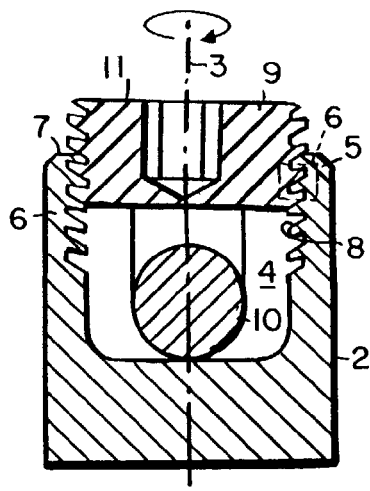
FIG. 5 shows a schematically illustrated holding element with inserted rod and loosely screwed in inner screw.
Figure 6:
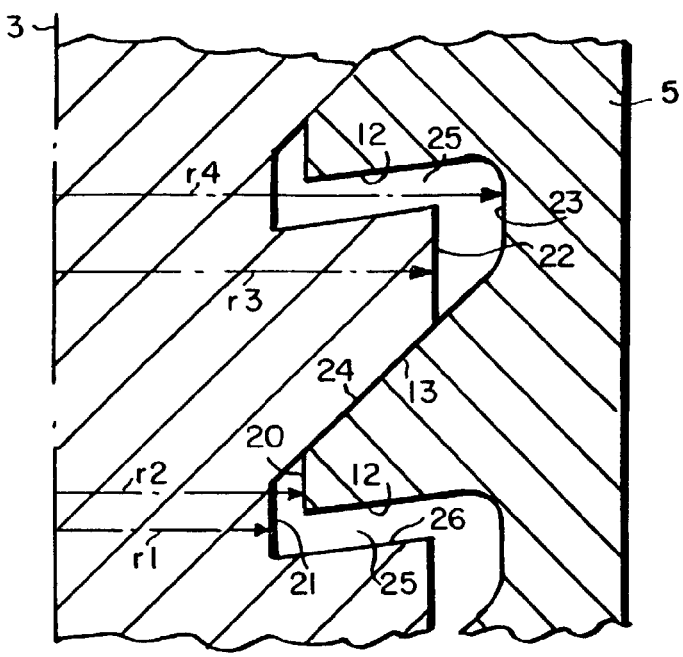
FIG. 6 shows the detail VI in FIG. 5 in enlarged scale.

In FIG. 5, as in FIG. 2, the head of the pedicle screw shown in FIG. 1 is shown with inserted rod and only initially inserted inner thread 9. In FIG. 6 section VI from FIG. 5 is illustrated in larger detail. As emerges from this enlarged illustration, the inner screw 9 and the outer thread of the legs 5 are dimensioned relative to one another as follows: radius $r_1$ from the centre of the screw coinciding with the longitudinal axis 3 to the base 21 of the thread of the screw 9 is smaller than radius $r_2$ from the central axis of the holding element coinciding with the symmetrical axis 3 to the tip of its spiral 20. Radius $r_3$ from the centre of the screw coinciding with the longitudinal axis 3 to the tip of the spiral 22 of the screw 9 is smaller than radius $r_4$ from the central axis of the holding element coinciding with the longitudinal axis 3 to the base 23 of the thread of its inner thread.

As can be seen in particular in FIG. 6, when screw 9 and exposed legs 5, 6 of the holding element are brought into engagement without load, when the cooperating flanks 13 of the inner thread and 24 of the screw, having the positive flank angles, are adjacent to one another there is a gap 25 between the flanks 12, 26, having a negative flank angle, facing one another in each case.

Figure 7:
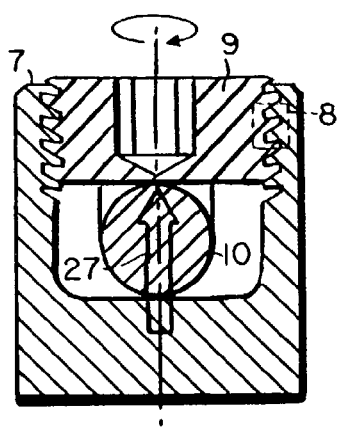
FIG. 7 shows the illustration corresponding to the illustration shown in FIG. 5 after the inner screw has been tightened.
Figure 8:
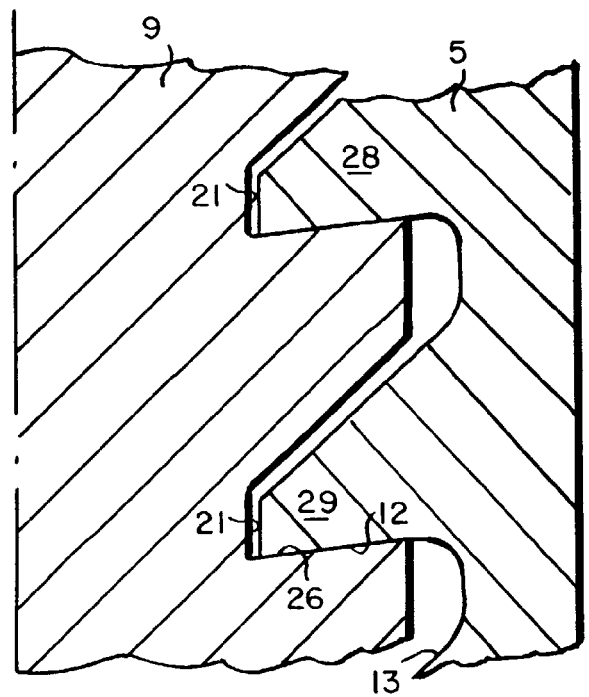
FIG. 8 shows the detail VIII shown in FIG. 7 in enlarged scale.

FIG. 7 shows the same object as in FIGS. 5 and 6, wherein the screw 9 is now screwed inwards far enough for it to press on the rod 10 and thereby to effect a counter-force, indicated by the arrow 27, on the screw 9. As a result of this, as can be seen in FIG. 8, the flanks 12, 26 facing one another in each case thereby end up on top of one another at a negative flank angle $\beta_2$, whereby the spirals 28, 29 of the inner thread are drawn inwards towards the respective base 21 of the pitches of the thread of the screw 9 in the manner shown in FIG. 8, with the result that the exposed legs are biased not outwards but inwards.

In a preferred embodiment the difference between the measurement of radii $r_1$ and $r_2$ is about 1 to 5% of the outer diameter of the thread or 0.1 to 0.5 mm with a screw diameter of 5 to 12 mm.

The invention claimed is:
1. A device comprising:
a shank;
a holding component for engaging and holding a rod, the holding component comprising a recess having two legs, a U-shaped cross-section for accommodating the rod, an open end for receiving the rod into the U-shaped cross-section between the legs, and an inner thread on the legs; and
a screw, which cooperates with the inner thread of said legs and acts on the rod when positioned in the recess, the screw having a central axis;
wherein the inner thread comprises an inner thread base, first and second partial flanks adjacent to one another, and an internal thread edge between the first and second partial flanks said second partial flanks facing away from said open end;
wherein the screw has an outer thread for engagement with the inner thread of said legs, the outer thread comprising an outer thread base, third and fourth partial flanks adjacent to one another, and an external thread edge between the third and fourth partial flanks said third partial flanks facing toward the open end;

the second and third partial flanks have a negative angle $\beta_2$ with a plane extending through the thread base and perpendicularly to the central axis;

the first and fourth partial flanks have a positive angle $\beta_1$ with a plane extending through the thread base, perpendicularly to the central axis; and wherein a first radius ($r_1$) from the central axis to the outer thread base is smaller than a second radius ($r_2$) from the central axis to the internal thread edge when the screw is engaged in the holding component, and a third radius ($r_3$) from the central axis to the outer thread edge is smaller than a fourth radius ($r_4$) from the central axis to the inner thread base; and when the screw and legs of the holding component are brought into engagement without load, the first and fourth partial flanks are in contact with one another, and a gap is provided between the second and third partial flanks wherein during the tightening of the screw into the holding component, a force between said legs and outer thread draws the legs inwards to prevent loosening of the connection between said rod and said screw.

2. The device according to claim 1, wherein the internal thread base is rounded between adjacent first and second partial flanks.

3. A device comprising:

a shank;

a holding component for engaging and holding a rod, the holding component comprising a recess having a U-shaped cross-section with two legs, an open end for receiving said rod into the recess, and an inner thread on the legs; and a screw to be screwed in between the legs and which acts on the rod when tightened in the recess, the screw having a central axis and an outer thread;

wherein the inner thread on the holding component and the outer thread on said screw each have thread flanks, a thread edge between adjacent thread flanks and a thread base;

wherein the thread flanks of the inner thread facing away from the open end and the thread flanks of the outer thread cooperating therewith have a negative angle $\beta_2$ with a plane extending through the thread base and perpendicularly to said central axis; and wherein the inner thread and the outer thread are dimensioned so that when the screw is engaged in the holding component without load there is a radial play between the inner and the outer thread and a gap between the thread flanks of the inner thread and the outer thread facing each other and having the negative flank angle, wherein during tightening of the screw, a force between said legs and outer thread draws the open end inwards to prevent loosening of the connection between said rod and said screw.

4. A device comprising:

a shank;

a holding component for engaging and holding a rod, the holding component comprising a recess having two legs, a U-shaped cross-section for accommodating said rod, an open end for receiving the rod into the U-shaped cross-section between the legs, and an inner thread on the legs; and a screw, which cooperates with the inner thread and acts on the rod when positioned in the recess, the screw having a central axis;

wherein the inner thread comprises an inner thread base, first and second partial flanks adjacent to one another, and an internal thread edge between the first and second partial flanks said second partial flanks facing away from said open end;

wherein the screw has an outer thread for engagement with the inner thread of the legs, the outer thread comprising an outer thread base, third and fourth partial flanks adjacent to one another, and an external thread edge between the third and fourth partial flanks said third partial flanks facing toward the open end;

the second and third partial flanks having a negative angle $\beta_2$ with a plane extending through the thread base and perpendicularly to the central axis;

the first and fourth partial flanks having a positive angle $\beta_1$ with a plane extendings through the thread base and perpendicularly to the central axis;

when the screw and legs of the holding component are brought into engagement without load, the first and fourth partial flanks are in contact with one another, and a first gap is provided between the second and third partial flanks, and a second gap is provided between the internal thread edge and the outer thread base, wherein during the tightening of the screw, a force between said legs and outer thread draws the legs inwards to prevent loosening of the connection between said rod and said screw.

5. A device comprising:

a shank;

a holding component for engaging and holding a rod, comprising a recess having a U-shaped cross-section with two legs, an open end for receiving the rod into the recess, and an inner thread on the legs;

a screw to be screwed in between the legs which acts on the rod when positioned in the recess, the screw having a central axis and an outer thread;

wherein the inner thread and the outer thread each have thread flanks, a thread edge between adjacent thread flanks and a thread base;

wherein the thread flanks of the inner thread facing away from the open end and the thread flanks of the outer thread cooperating therewith have a negative angle $\beta_2$ with a plane extending through the thread base and perpendicularly to said central axis;

wherein the inner thread and the outer thread are dimensioned so that when the screw is engaged in the holding component without load there is a radial play between the inner and the outer thread and a gap between the thread flanks of the inner thread and the outer thread facing each other and having the negative flank angle, and a second gap between the internal thread edge and the outer thread base, wherein a force between said legs and outer thread draws the legs inwards to prevent loosening of the connection between said rod and said screw.

* * * * *

UNITED STATES PATENT AND TRADEMARK OFFICE
CERTIFICATE OF CORRECTION

PATENT NO. : 7,018,378 B2
APPLICATION NO. : 10/098937
DATED : March 28, 2006
INVENTOR(S) : Biedermann et al.

It is certified that error appears in the above-identified patent and that said Letters Patent is hereby corrected as shown below:

On the Title Page

Item (75) Inventors, line 2     Delete "Dezsö Jeszensky, St. Gallen (DE)",
                                Insert -- Dezsö Jeszensky, St. Gallen (CH) --

In the Claims

Column 6, line 19, Claim 4      Delete "extendings",
                                Insert --extending--

Signed and Sealed this

Thirteenth Day of February, 2007

JON W. DUDAS
*Director of the United States Patent and Trademark Office*